(12) United States Patent
Serowski

(10) Patent No.: US 6,584,977 B1
(45) Date of Patent: Jul. 1, 2003

(54) COMBINED PATIENT INTERFACE AND EXHAUST ASSEMBLY

(75) Inventor: Andrew Serowski, Plantsville, CT (US)

(73) Assignee: Respironics, Inc., Murrysville, PA (US)

( * ) Notice: Subject to any disclaimer, the term of this patent is extended or adjusted under 35 U.S.C. 154(b) by 18 days.

(21) Appl. No.: 09/824,291

(22) Filed: Apr. 2, 2001

Related U.S. Application Data
(60) Provisional application No. 60/195,020, filed on Apr. 6, 2000.

(51) Int. Cl.$^7$ .............................................. A62B 18/08
(52) U.S. Cl. .............................. 128/206.24; 128/207.12
(58) Field of Search ..................... 128/206.21, 206.23, 128/206.24, 206.26, 206.27, 206.28, 207.11, 207.12, 207.13, 205.27, 206.12, 206.15, 206.18, 205.24, 912

(56) References Cited

U.S. PATENT DOCUMENTS

| | | | |
|---|---|---|---|
| 1,615,718 A | * | 1/1927 | Olgard ................... 128/201.15 |
| 2,551,653 A | * | 5/1951 | Wildhack ............... 128/201.15 |
| 2,684,066 A | * | 7/1954 | Glidden ................. 128/201.15 |
| 3,429,342 A | | 2/1969 | Garrett |
| 3,467,136 A | | 9/1969 | Masson |
| 3,474,831 A | | 10/1969 | Noakes |
| 3,478,571 A | | 11/1969 | Dugay |
| 3,592,237 A | | 7/1971 | Borschers |
| 3,669,108 A | | 6/1972 | Sundblom et al. |
| 3,770,014 A | | 11/1973 | Limberg |
| 3,796,216 A | * | 3/1974 | Schwarz ................ 128/205.13 |
| 3,948,289 A | | 4/1976 | Stephens |
| 3,951,379 A | | 4/1976 | Cornelius |
| 4,057,059 A | | 11/1977 | Reid et al. |
| 4,077,404 A | * | 3/1978 | Elam ...................... 128/204.28 |
| 4,182,371 A | | 1/1980 | Moore |
| 4,234,013 A | | 11/1980 | Rikuta |
| 4,245,631 A | * | 1/1981 | Wilkinson et al. ..... 128/203.27 |
| 4,274,404 A | * | 6/1981 | Molzan et al. ......... 128/204.25 |
| 4,280,527 A | | 7/1981 | Pease |
| 4,351,510 A | | 9/1982 | Welker |
| 4,354,516 A | | 10/1982 | Newell |
| 4,428,397 A | | 1/1984 | Bron |
| 4,655,213 A | * | 4/1987 | Rapoport et al. ...... 128/205.25 |
| 5,065,756 A | | 11/1991 | Rapoport |

(List continued on next page.)

FOREIGN PATENT DOCUMENTS

| | | |
|---|---|---|
| CA | 518925 | 11/1955 |
| DE | 27 48 055 | 10/1977 |
| GB | 816212 | 7/1959 |
| SU | 623186 | 8/1975 |
| SU | 1015344 | 4/1983 |
| WO | WO 82/03548 | 10/1982 |

OTHER PUBLICATIONS

Product Literature, "7200 Series" Puritan Bennet, Jun. 1988.
Product Literature, "7200a Option #50 Flow–By" Puritan Bennet, Jan. 1987.
"Effects on the Work of Breathing: Flow Triggering Versus Pressure Triggering," Puritan Bennet, Nov. 1989.

Primary Examiner—Weilun Lo
Assistant Examiner—Teena Mitchell
(74) Attorney, Agent, or Firm—Michael W. Haas (57) ABSTRACT

A combined patient interface and integrated exhaust assembly that passes a controlled flow of gas from an interior of a patient interface to ambient atmosphere at a predetermined flow rate irrespective of variations of pressure in the interior of the patient interface device relative to ambient atmosphere. Control of the flow of exhaust gas is achieved by varying the effective cross sectional area of the exhaust path communicating the interior of the patient interface with ambient atmosphere based on the pressure in the interior of the patient interface relative to ambient atmospheric pressure.

23 Claims, 4 Drawing Sheets

U.S. PATENT DOCUMENTS

| | | |
|---|---|---|
| 5,148,802 A | 9/1992 | Sanders et al. |
| 5,161,525 A | 11/1992 | Kimm et al. |
| 5,239,995 A | 8/1993 | Estes et al. |
| 5,318,019 A * | 6/1994 | Celaya .................. 128/204.26 |
| 5,323,772 A | 6/1994 | Linden et al. |
| 5,411,021 A * | 5/1995 | Gdulla et al. .......... 128/206.17 |
| 5,507,282 A | 4/1996 | Younes |
| 5,540,220 A | 7/1996 | Gropper et al. |
| 5,542,416 A | 8/1996 | Chalvignac |
| 5,645,049 A * | 7/1997 | Foley et al. ............ 128/200.23 |
| 5,655,520 A | 8/1997 | Howe et al. |
| 5,657,752 A | 8/1997 | Landis et al. |
| 5,662,101 A * | 9/1997 | Ogden et al. ........... 128/202.27 |
| 5,685,296 A | 11/1997 | Zdrojkowski et al. |
| 5,937,855 A | 8/1999 | Zdrojkowski et al. |
| 6,192,886 B1 * | 2/2001 | Rudolph ................. 128/205.25 |
| 6,206,003 B1 * | 3/2001 | Burch .................... 128/206.21 |
| 6,435,181 B1 * | 8/2002 | Jones et al. ............. 128/204.18 |

* cited by examiner

COMBINED PATIENT INTERFACE AND EXHAUST ASSEMBLY

CROSS-REFERENCES TO RELATED APPLICATIONS

This application claims priority under 35 U.S.C. § 119(e) from provisional U.S. patent application Ser. No. 60/195,020 filed Apr. 6, 2000.

BACKGROUND OF THE INVENTION

1. Field of the Invention

The present invention pertains to a combined patient interface and integrated exhaust assembly, and, in particular, to such a combination in which the exhaust assembly provides a controlled flow of exhaust gas, such as a constant flow of gas, from the interior of the patient interface over a range of pressures within the patient interface relative to ambient atmosphere.

2. Description of the Related Art

Conventional exhaust assembles are used, for example, to provide an exhaust flow path for exhaled air in a ventilation circuit, which supplies a continuous flow of breathing gas to a spontaneously breathing patient. During the exhalation phase of the patient's breathing, exhalation gas backflows in the ventilation circuit and, unless exhausted from the circuit, can be rebreathed by the patient during the next inhalation phase. Rebreathing of exhaled gas is undesirable, of course, because the exhalation flow contains $CO_2$. Reliable and thorough exhaustion or purging of exhalation gas from the ventilation circuit is, thus, an important feature of such ventilation circuits, which are also commonly referred as breathing circuits or patient circuits. This purging becomes a more difficult problem the further the exhalation valve is located from the patient interface, due to the amount of residual exhaled gas in the intervening ventilation circuit dead space.

Most such exhalation valves provide varying fluid flow at varying fluid pressures. However, the naturally occurring relationship of fluid flow rate to pressure (flow is proportional to the square root of pressure) may be unacceptable in a ventilation circuit for a number of reasons. For example, in medical ventilators used to assist patient breathing, and in similar devises used to supply breathing gas to a spontaneously breathing patient, it has been common practice to include a fixed size leak, especially in single limb circuits, to flush away the gas that is exhaled by the patient into the breathing circuit before the exhaled gas can be rebreathed by the patient with the next inhalation. The fixed sized, i.e., fixed geometry or fixed orifice, leak may be provided by an exhalation valve. However, an exhalation valve with a flow characteristic that varies naturally with pressure variations in the patient circuit may not be suitable as a patient circuit exhaust valve.

Additionally, in the operation of such systems it is known to supply to a patient an exhalation pressure that is lower than the inhalation pressure. With many conventional exhalation valves, the size of the fixed leak needed to flush exhaled gas from the circuit under the relatively lower pressure of exhalation may be so large that the flow rate through the fixed leak at the higher inhalation pressure would result in enormous waste of supply gas during inhalation. Such conditions may also require a larger capacity pressure generator, commonly a blower, for example, than would otherwise be required. This too is wasteful in that the result is unnecessary added cost for the apparatus and increased energy consumption to operate it.

It is, therefore, preferable that the flow rate of the leak provided to flush exhaled gas from such a ventilation circuit does not change appreciably within the range of pressures applied in the circuit. In this sense, a fixed leak is more desirably one that provides a fixed flow rate, than one characterized by a flow path cross sectional area of fixed size.

Among the prior art of valves purporting to regulate flow by means of pressure actuated regulators are those disclosed in U.S. Pat. Nos. 3,467,136, 3,474,831, 3,592,237, 3,948,289 and 3,951,379. Other flow regulating valves are disclosed in U.S. Pat. Nos. 3,429,342, 3,473,571, 3,770,104, 4,182,371, 4,234,013, 4,280,527, 4,351,510 and 4,354,516. U.S. Pat. No. 4,428,397, apparently related German Patent no. DE 27 48 055 A1, and Russian Patent abstract SU 1015344A disclose a valve for controlling the rate of flow of fluid therethrough. In addition, U.S. Pat. No. 5,002,050 discloses a medical gas flow control valve and U.S. Pat. No. 5,438,981 discloses an automatic safety valve and diffuser for a nasal and/or oral gas delivery mask.

U.S. Pat. Nos. 5,685,296 and 5,937,855 disclose a flow regulating valve that exhausts gas from a ventilation circuit at a constant flow rate despite varying pressure in the ventilation circuit. However, as noted above, it may be further desirable to locate the exhaust valve at the mask, for example, so that the amount of ventilation circuit dead space is minimized and to eliminate the need to provide a relatively bulky exhaust structure on the ventilation circuit. In treating obstructive sleep apnea OSA, for example, a positive pressure therapy is provided to the patient while he or she sleeps. Therefore, it is preferable for the patient circuit to be flexible and readily movable during the pressure support treatment. This goal may be frustrated by providing the exhaust valve on the patient circuit. In the hospital setting, it is also preferable to minimize the entanglements on the patient circuit to keep as clear a working area as possible for the doctors and nurses.

SUMMARY OF THE INVENTION

Accordingly, it is an object of the present invention to provide a combined patient interface and integrated exhaust assembly that overcomes the shortcomings of conventional flow control valves. More specifically, the present invention contemplates a novel combination of a patient interface, such as a mask, and a flow control valve integrated with the mask and/or integrated with connection between the mask and the patient circuit. In a preferred embodiment of the present invention, the flow control valve exhausts gas from the mask at a constant gas flow rate over a range of pressures within the interface. Because the valve is incorporated into the breathing mask or similar apparatus, which confronts the face of the patient, the amount of dead space in the patient circuit is minimized, and there is no excess material on the patient circuit that can hinder its performance or comfort.

This object is achieved according to one embodiment of the present invention by providing a patient interface and exhaust assembly in which the patient interface assembly includes a faceplate having a first opening defined in a first end and a second opening defined in a second end thereof. A seal associated with the second opening is provided for contacting a surface of the patient, with the faceplate, seal, or both defining an interior of the patient interface assembly. A patient circuit is coupled to the first opening to communicate with an interior of the patient interface assembly. In this embodiment, the exhaust assembly is provided at the interconnection of the faceplate and patient circuit, and includes an exhaust path defined generally between the faceplate and the patient circuit and a flow regulating member. In another embodiment of the present invention, the exhaust assembly is incorporated into the mask shell or faceplate itself with the exhaust path being defined between portions of the faceplate and between the flow regulating member and a portion of the faceplate.

In either embodiment, the flow regulating member controls the rate of flow of exhaust gas passing to atmosphere through the exhaust path by being deformed into the exhaust path varying degrees. The degree of deformation of the flow regulating member into the exhaust path is based on a pressure in the interior of the patient interface assembly relative to ambient atmospheric pressure. More specifically, the flow regulating member responds to the different pressures applied to its opposite sides to vary the effective cross sectional area of the exhaust path. With relatively higher pressure within the patient interface relative to ambient atmosphere pressure, the flow regulating member flexes and deforms into the flow path, thereby narrowing the exhaust path and thus reducing its effective cross sectional area.

The amount of narrowing of the exhaust path, and, thus, the amount of cross sectional area reduction, varies with variation in the elevated pressure within the patient interface. Higher pressures in the patient interface produce greater exhaust path area reduction and lower pressures produce smaller flow path area reduction. By providing a greater exhaust path area reduction in the presence of high patient circuit pressures and a lower exhaust path area reduction in the presence of lower patient circuit pressure, the flow rate of the exhaust gas can be kept substantially constant over these ranges of pressures in the patient circuit. Because the flow regulating member can flex to an infinite number of positions with incremental changes in the elevated gas pressure within the patient interface, the cross sectional area of the exhaust path can be any of a corresponding infinite number of values. Hence, with this exhaust valve assembly it is possible to provide relatively constant exhaust flow over a continuous range of operating pressures. It is also possible to provide other flow rate profiles over the range of operating pressures, such as a decreased flow as pressure increases, that cannot be achieved by a fixed size leak.

Further objects of the present invention are to provide a system and method for providing a supply of breathing gas to an airway of a patient that makes use of the combined patient interface and integrated exhaust assembly.

These and other, features and characteristics of the present invention, as well as the methods of operation and functions of the related elements of structure and the combination of parts and economies of manufacture, will be more apparent upon consideration of the following detailed description and the accompanying drawings, all of which form a part of this specification. It is to be expressly understood that the drawings are for the purpose of illustration and description only and do not represent or define the limits of the invention. Nor is the size, scale or proportion of any elements shown in the drawings intended to reflect the actual size, scale or proportion thereof. Moreover, in the various figures identical parts are designated by identical reference numerals, and similar parts are designated by the same reference numerals primed.

DETAILED DESCRIPTION OF THE PRESENTLY

PREFERRED EXEMPLARY EMBODIMENTS

Figure 1:
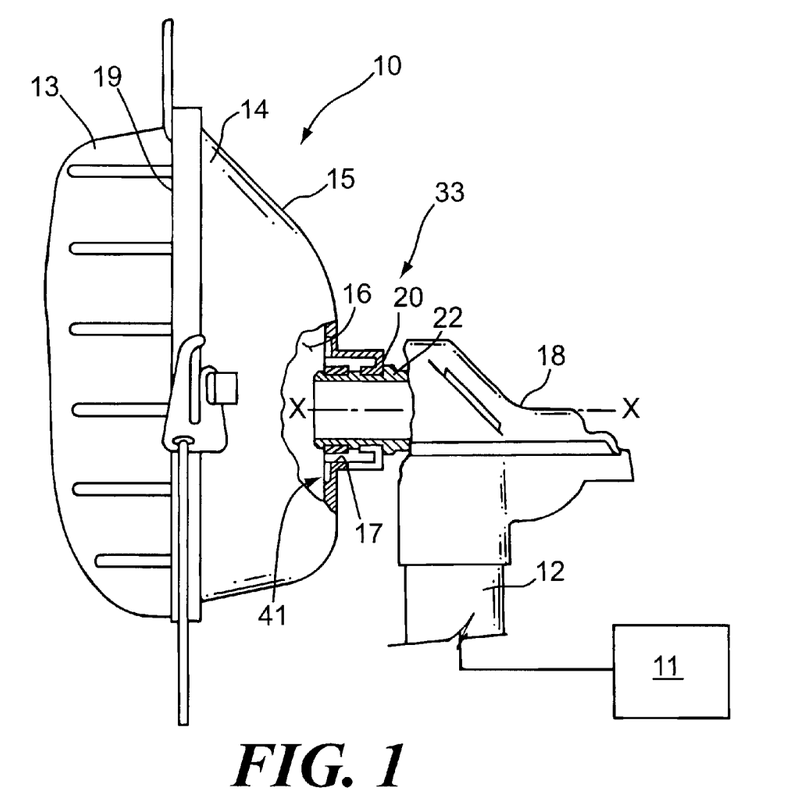
FIG. 1 is a side elevation of a patient interface and a connected gas supply circuit, partially sectioned to show the exhaust assembly according to a first embodiment of the present invention.

There is generally indicated at 10 in FIG. 1 a patient interface assembly for communicating a flow of breathing gas produced by a pressure generator 11 and carried by a patient circuit 12 to an airway of patient (not shown). As the prior art is replete with descriptions of patient circuits and various types of pressure generators, including CPAP devices, bilevel devices, autotitration devices, ventilators, and even a tank of pressurized gas, no further description of these items is necessary for present purposes. In the illustrated embodiment, patient interface assembly 10 preferably comprises either a full or partial face mask 14 that fits over at least part of the patient's face, including the mouth, the nares, or both for communicating a flow of breathing gas from the gas source to an airway of a patient. In the illustrated embodiment, patient interface assembly 10 includes a faceplate 15 and a seal 13 for contacting the surface of the patient. Faceplate 15, seal 13, or both define an interior space 16 of mask 14 that receives the patient's nose or other facial features when the mask is donned by the patient.

Faceplate 15 is preferably, but not necessarily, a rigid material, such as plastic, and seal 13, in this embodiment, is defined by flexible, relatively soft material to maximize patient comfort. The specific composition of faceplate 15 and seal 13 are generally not relevant to the present invention so long as suitable materials that allow the invention to operate as described below are selected. Faceplate includes a first opening 17 to which patient circuit 12 is attached, and a second opening 19 to which seal 13 is attached. In an exemplary embodiment, seal 13 and faceplate 15 are separate structures that are combined or joined during the manufacturing process to form patient interface assembly 10. However, the present invention contemplates other structures for mask 14, such as both faceplate 15 and seal 13 being made from like materials. In general, however, a nasal mask or nasal/oral mask suitable for use with the present invention will have a seal portion that contacts the patient and a faceplate portion that carries the seal, with the exact structure, shape, and composition of the seal and faceplate not being particularly relevant to the present invention.

In the illustrated embodiment, breathing gas is directed from patient circuit 12 to interior space 16 via a suitable connecting element 18. In this embodiment, connecting element is a 90° elbow that rotateably couples patient circuit 12 to faceplate 15 at a swivel connection 20. Swivel connection 20 allows free swiveling of connecting element 18 with respect to mask 14 about axis x—x. It is to be understood, however, that the present invention contemplates a variety of configurations for connecting element 18, other than the 90° elbow shown in FIG. 1, such as an elbow of less than 90°. The present invention also contemplates coupling patient circuit 12 directly to mask 14 without connecting element 18.

Figure 2:
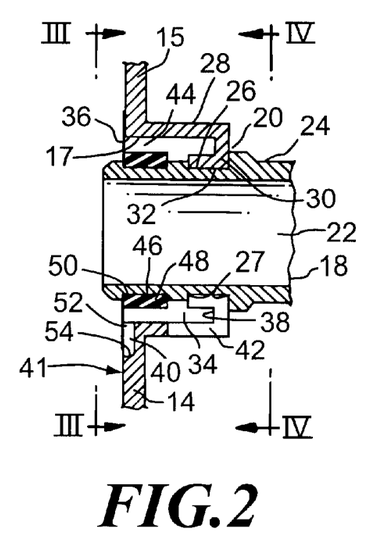
FIG. 2 is an enlarged, sectional view of the first embodiment of the exhaust assembly of the present invention taken along lines II—II of FIG. 3.

Referring, more particularly, to FIGS. 1 and 2, a supply tube 22 of connecting element 18 opens into interior space 16 of mask 14. An external surface 24 of supply tube 22 includes a reduced diameter cylindrical swivel bearing groove or recess portion 26 that extends circumferentially about tube 22 to form a bearing surface for swiveling engagement with mask faceplate 15. The cooperating part of mask faceplate 15 includes an outwardly projecting, generally tubular extension 28, and a smaller diameter swivel bearing portion 30, both of which coaxially enclose supply tube 22. Swivel bearing portion 30 includes a cylindrical swivel bearing surface 32 that cooperably engages cylindrical recess 26, and is captured by axially opposed shoulders 27 formed at the opposed axial ends of recess 26 to thereby retain swivel bearing surfaces 26 and 32 in swiveling, mutually engaged relationship. Accordingly, connector element 18 is retained for free swiveling action about axis x—x with respect to faceplate 15.

An exhaust assembly, generally indicated at 33, for venting gas from interior space 16 of patient interface assembly 10 will now be described. An annular space 34 is formed radially between tubular extension 28 and tube 22, and extends axially between an inner end 36, which opens to interior space 16, and an outer end 38 located outside of the confines of faceplate 15. Annular space 34 thus defines a part of an exhaust path 44 between interior space 16 and the ambient atmosphere. Regarding other portions of exhaust path 44, at its inner end 36 annular space 34 communicates with interior space 16 via a plurality of circumferentially spaced, radially outwardly projecting grooves 40. In the exemplary embodiment illustrated in FIG. 3, six symmetrically disposed grooves are formed into an inner surface 41 of faceplate 15 about first opening 17. At a location suitably disposed outside the confines of faceplate 15, annular space 34 communicates with the ambient atmosphere via a plurality of circumferentially spaced exhaust openings 42. See FIGS. 2 and 4. Exhaust openings 42 preferably are located and configured to direct exhaust gas flow away from the face of the patient, to thereby minimize the discomfort of gas flow impinging on the patient's skin.

Grooves 40, annular space 34, and exhaust openings 42 together define exhaust path 44 through which gases exhaled by the patient, for example, are exhausted to the ambient atmosphere, rather than backflowing in patient circuit 12 and being subsequently rebreathed by the patient. Exhaust path 44 also serves to vent to ambient atmosphere excess gas delivered by the pressure generator.

The described structure, however, is more than merely a suitably located exhaust assembly. A unique, flow rate control function is also provided to ensure an essentially constant exhaust flow rate through exhaust assembly 33 throughout a range of pressure differentials across the exhaust assembly, i.e., between interior space 16 and ambient atmosphere. Because the ambient pressure is constant for all practical purposes, a constant exhaust flow rate over a range of pressure differentials means essentially a constant exhaust flow rate over a range of pressures within patient interface assembly 10. Such a range of pressures will routinely be observed in mask 14, not only because patient breathing effort will generate pressure differences between inhalation and exhalation, but in addition because ventilation systems often are programmed to supply differing levels of pressure in coordination with the patient's breathing. For example, it is known to operate pressure generator 11 in a bilevel mode to deliver a high pressure to the patient during inspiration than during expiration. See, e.g., U.S. Pat. Nos. 5,148,802 and 5,443,193 the contents of which are hereby incorporated by reference into the present application.

Figure 3:
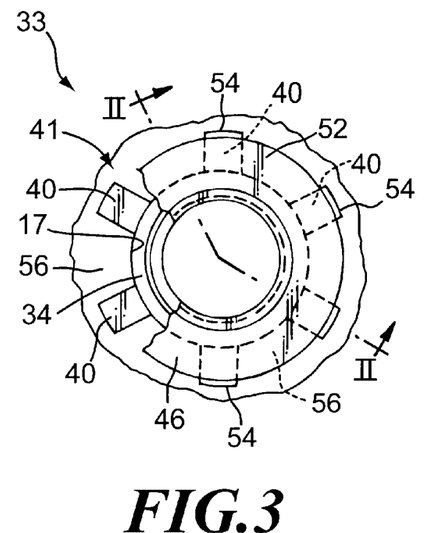
FIG. 3 is an elevation of the exhaust assembly of FIGS. 1 and 2 shown from within the interior of the patient interface along lines III—III of FIG. 2, and with a portion of the flow regulating member broken away to reveal the valve porting.
Figure 4:
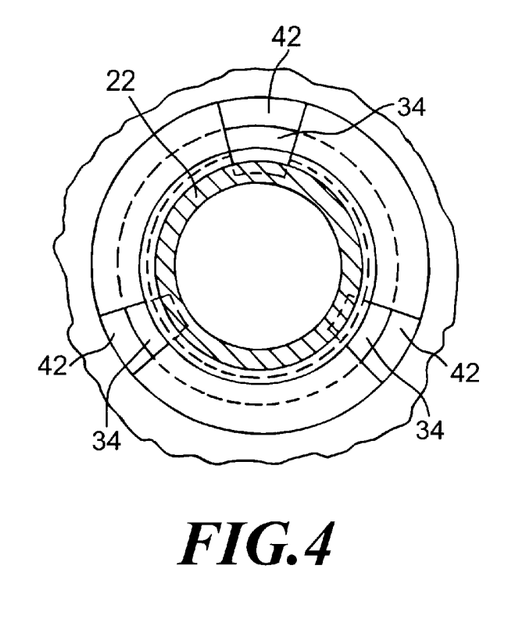
FIG. 4 is an elevation of the valve of FIGS. 1 and 2 shown from outside the patient interface taken along lines IV—IV of FIG. 2.

Referring to FIGS. 2 and 3, exhaust assembly 33 includes a flow regulating member 46 which, in a preferred embodiment, is a resiliently deformable membrane, is provided within space 16 in an overlying relationship with grooves 40. The present invention contemplates that membrane 46 is any one of a variety of deformable materials, such as silicone rubber, that enables the membrane to deform into exhaust path 44 so as to alter the effective area of the path. In the illustrated embodiment, membrane 46 includes a cylindrical portion 48 that is sealingly engaged in a circumferential recess 50 formed on the exterior, cylindrical surface 24 of supply tube 22 at a location spaced axially inward of recess 26. At the axially innermost end of cylindrical portion 48, an annular flap portion 52 of membrane 46 extends radially outward to a location just short of the radially outermost extent of grooves 40, thus leaving a radially outermost terminal end portion 54 of each groove 40 that is not overlain by membrane 46. The exposed ends 54 of grooves 40 thus serve an inlet to exhaust path 44 for gas venting to atmosphere. The portions of flap 52 disposed circumferentially between adjacent grooves 40 are supported on the corresponding intervening portions 56 of interior surface 41 of faceplate From the above description, it can be appreciated that the pressure differential across membrane flap 52 created by the difference between the elevated pressure within interior space 16 and the pressure of the ambient atmosphere outside of mask 14 will tend to force the resiliently deformable membrane flap 52 into grooves 40, thereby diminishing the effective cross-sectional area of exhaust path 44 a predeterminable amount. The amount by which the effective cross-sectional area of exhaust path 44 is diminished will depend on the magnitude of the pressure differential to which membrane flap 52 is subjected. When the pressure differential increases, flap 52 is deformed into grooves 40 by a further increment, thereby decreasing the exhaust flow path cross sectional area, and when the differential pressure decreases, flap 52 recoils, thus, increasing the exhaust path cross sectional area.

The geometry, dimensions and material properties, such as the durometer, of membrane 46, exhaust path 44, or each groove in the exhaust path are selected to provide the desired control over the flow rate of the exhaust path over the range of pressures in the patient circuit. For example, the present invention contemplates that exhaust path cross sectional area diminishes and increases such that, in response to increasing and decreasing pressure differentials, respectively, the exhaust flow rate remains essentially constant over a range of expected ventilation circuit pressures. The specific configurations shown in the figures are provided for illustration purposes and are not intended to be the only possible configuration for accomplishing this function. For example, the present invention contemplates increasing or decreasing the number of grooves 40 defined in faceplate 15. It should be noted that membrane may rotate with supply tube 22 as the connection element 18 swivels with respect to mask 14. This will not effect operation of the described valving function since both the membrane 46 and the exhaust flow path, including grooves 40, are symmetrically arranged about axis x—x.

The present invention also contemplates that flow regulating member 46 need not be formed from a unitary piece of material, but may be defined by a plurality of pieces of membrane material, each overlying a respective groove to provide the above-described flow regulating capability. Furthermore, piece of material can be coupled to faceplate 15, rather than supply tube 22, to allow supply tube 22 to rotate relative to mask 14.

The present invention further contemplates that the connection of supply tube 22 to faceplate 15 need not be a rotational connection. In which case, any one of a variety of techniques can be used to interlock supply tube 22 to the faceplate and the flow regulating member can be provided on either the supply to of the faceplate. If a rotational capability is desired for patient circuit relative to the patient interface assembly, a rotational coupling can be provided in elsewhere in the patient circuit.

It should be noted that the present invention contemplates controlling the flow rate of the exhaust gas over the range of operating pressures such that the flow rate is not necessarily constant. For example, it may be desirable that the flow rate of the exhaust gas decrease as the pressure in the patient circuit increases. The shape and size of the exhaust path and/or the shape, size, durometer, resiliency, elasticity or other properties of the flexible membrane can be selected to achieve such an exhaust gas flow rate versus patient circuit pressure relationship.

Figure 5:
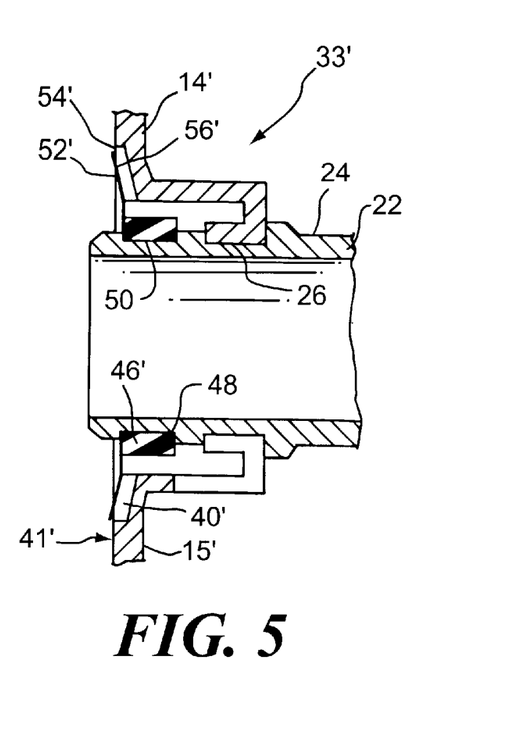
FIG. 5 is a sectional view similar to FIG. 2 showing an alternative embodiment of exhaust assembly of the invention.

FIG. 5 illustrates an alternative embodiment of an exhaust assembly 33' that is similar in all salient respects to exhaust assembly 33 of FIGS. 1–4, excepting only differences in the configuration of flow regulating member 46' the structures of faceplate 14' with which the flow regulating member cooperates. For example, flow regulating member 46' is a resiliently deformable membrane that is disposed in overlying relationship with grooves 40, as with the embodiment of FIGS. 1–4. Membrane 46' comprises a cylindrical portion 48 that is sealingly engaged in a circumferential recess 50 formed on the exterior, cylindrical surface 24 of supply tube 22 at a location spaced axially inward of swivel bearing recess 26. At the axially innermost end of cylindrical portion 48, an annular flap portion 52' of membrane 46' extends radially outward to a location just short of the radially outermost extent of grooves 40', thus leaving a radially outermost terminal end portion 54' of each groove 40' that is not overlain by membrane 46'. The portions of flap 52' disposed circumferentially between adjacent grooves 40' are supported on the corresponding intervening portions 56' of the faceplate interior surface 17'.

In this embodiment, however, flap 52' is angled axially inward, that is to the left as viewed in FIG. 5, to form a shallow conical shape. Grooves 40' are similarly angled, as are the intervening surface portions 56' of faceplate surface 41'. Apart from these differences, the FIG. 5 embodiment is essentially the same as the FIG. 1–4 embodiment. The alternative membrane and groove geometry of FIG. 5 is but one of any number of alternative configurations and structures that are intended to be included within the scope of the present invention.

Figure 6:
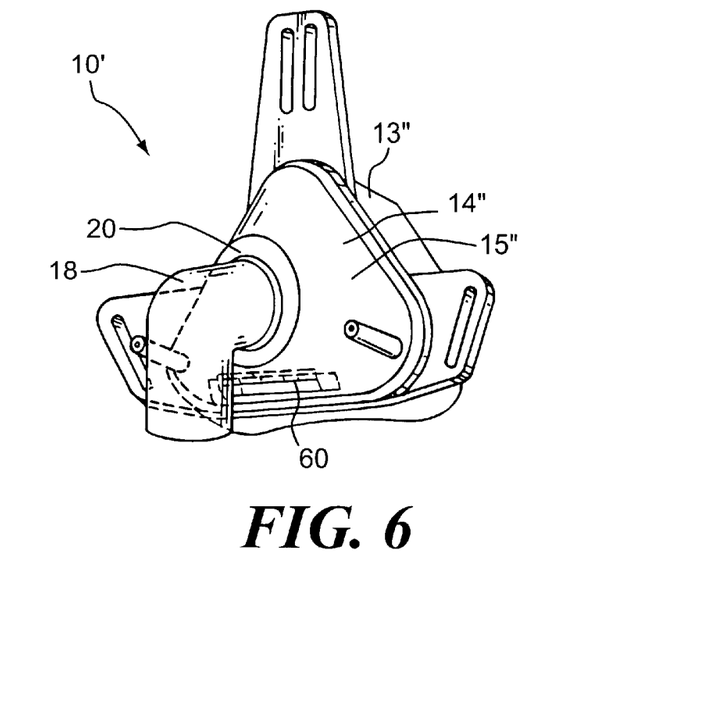
FIG. 6 is a perspective view of a patient interface with another alternative embodiment of the exhaust assembly of the present invention.

A further alternative embodiment of an exhaust assembly 60 is shown in FIGS. 6–10. In this embodiment, the exhaust assembly functions as above described. However, the exhaust path and cooperating elements are incorporated into faceplate 15" of patient interface assembly 10', rather than in swivel connection 20. In FIG. 6, patient interface assembly 10' includes a mask 14" coupled to a ventilator connection element 18, which may be connected to mask 14" by a swivel connection 20 or by a fixed connection. Mask 14" includes a faceplate 15" having an integral exhaust assembly 60 constructed into the faceplate, as described below with references to FIGS. 7–10.

Figure 7:
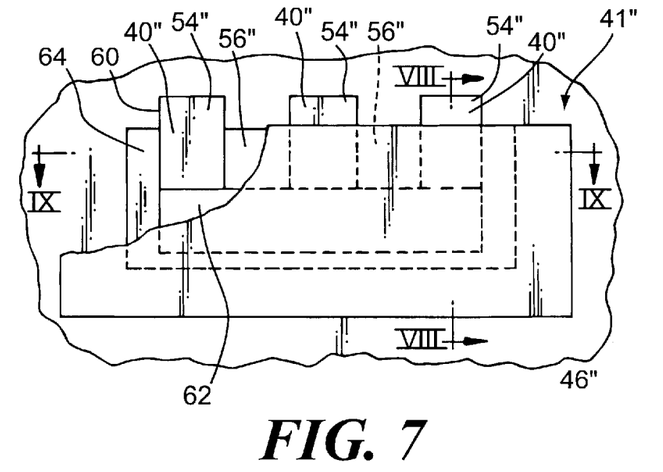
FIG. 7 is a fragmentary elevation view shown from within the patient interface of FIG. 6 showing the exhaust assembly of the FIG. 6 embodiment, with the flow regulating member partially broken away to reveal the valve porting.
Figure 8:
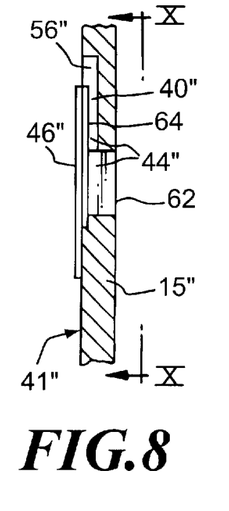
FIG. 8 is a sectional view taken on lines VIII—VIII of FIG. 7.
Figure 9:
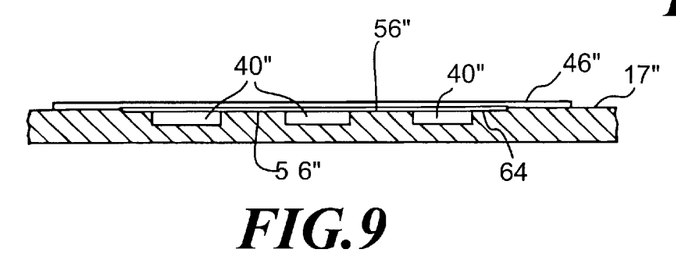
FIG. 9 is a sectional view taken on lines IX—IX of FIG. 7.
Figure 10:
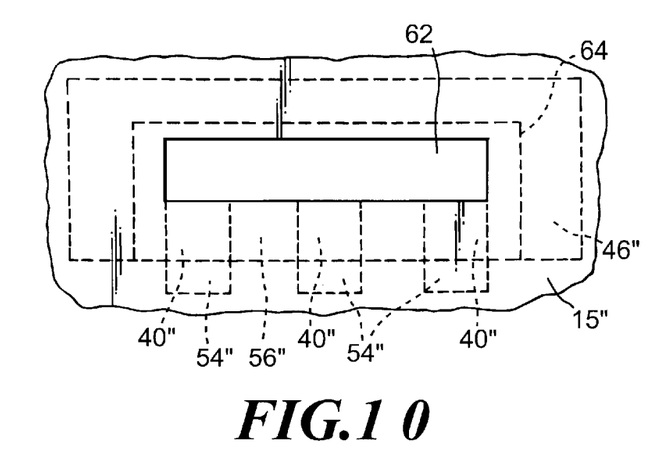
FIG. 10 is an elevation view shown from outside of the patient interface of FIG. 6, along lines X—X of FIG. 8.

In FIG. 7, exhaust assembly 60 is shown as seen from the inside of mask 14". FIG. 8 is a sectional view taken along line VIII—VIII of FIG. 7 showing the details of the exhaust assembly. The interior surface 41" of faceplate 15" has formed therein a plurality of elongated grooves 40" disposed in spaced apart relationship. Each groove 40" communicates with an elongated through opening 62 defined in faceplate 15", which communicates between the interior and the exterior of faceplate 15". Thus, grooves 40" and opening 62 together define an exhaust path 44" (see FIG. 8) for venting gas, such as the patient's exhalation flow, to the ambient atmosphere. A flow regulating member 46" in the form of a resiliently flexible membrane overlays opening 62 and a major portion of each groove 40", leaving a terminal end portion 54" of each groove 40" open to the interior of the mask. Between the grooves 40", membrane 46" overlies intervening portions 56" of surface 41".

An additional structural feature shown in FIGS. 7–10 is a shallow recess 64 formed in face plate interior surface 17" on a footprint that includes all of the described exhaust flow path except the terminal end portions 54" of grooves 40". The function of recess 64 is to aid in controlling the resilient deformation of membrane 46" into grooves 40". A recess similar to recess 64 may also be used with the FIG. 1–6 embodiments. It is thus another of a large variety of structural or geometric variations which are applicable for purposes of the invention.

Membrane 46" overlies recess 64 and is fixed to faceplate surface 41" by any suitable means, for example bonding thereof with adhesive placed outside the perimeter of recess 64. Screws or other mechanical fasteners may also serve the purpose. Thus secured, the membrane functions as above described with reference to the FIG. 1–6 embodiments to provide constant exhaust flow over a range of pressure differentials across the valve.

It can be appreciated that exhaust assembly 60 provides a constant flow rate or any predetermined relations for the flow rate of exhaust from the mask, thereby minimizing deadspace and optimizing the prevention of $CO_2$ rebreathing. In addition, exhaust assembly 60 has no external bulges or protrusions that may hinder or impede the use of the breathing gas system. It can be further appreciated that a variety of alternative configurations are possible for the various components of exhaust assembly 60. For example, the number of grooves 40" can be increased or decreased, the flow regulating member can be separated into individual elements associated with each groove, and multiple opening 62 can be provided. The present invention further contemplates that one opening 62 can be provided for each groove 40". In addition, the shape and depth of grooves 40", can be varied, as can the thickness, size, shape and material specification of the membrane 46".

Figure 11:
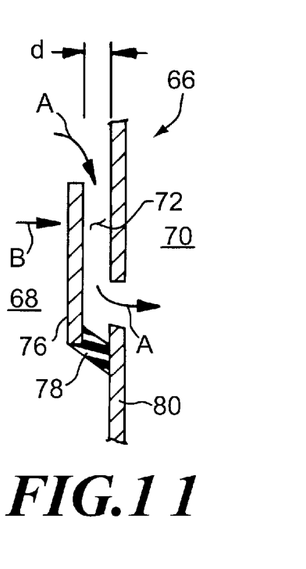
FIG. 11 is sectional view of a portion of a patient interface that includes yet another alternative embodiment of the exhaust assembly of the present invention.

FIG. 11 illustrates is sectional view of yet another embodiment of an exhaust assembly 66 for use in venting gas from an interior space 68 of patient interface to ambient atmosphere 70 through an exhaust path 72, as indicated by arrows A. In the exhaust assemblies in the above embodiments, the flow regulating member is a flexible membrane that deflects to control the size of the exhaust path as a function of the pressure within the patient interface. Exhaust assembly 66 also includes a flow regulating member 74. However, flow regulating member 74 is defined, at least in part, by a relatively rigid member 76 in addition to a flexible member 78 that allows for movement of rigid member 76. More specifically, the pressure differential across rigid member 76 created by the difference between the elevated pressure within interior space 68 and the pressure of the ambient atmosphere 70 tends to force the rigid member toward faceplate 80 as indicated by arrow B, thereby decreasing dimension d, hence, diminishing the effective cross-sectional area of exhaust path 72. Movement is rigid member 74 is possible due to the flexible nature of flexible member 78.

FIG. 11 clarifies that the flow regulating member need not be formed entirely from a flexible membrane. On the contrary, the present invention contemplates a variety of techniques for controlling the size of the exhaust path based on the gas pressure within the patient interface to control the flow of gas from the patient circuit. It should be understood that flexible member 78 in FIG. 11 can take the form of a spring, bellows, or any other member that provides a resiliently flexible characteristic, allowing a portion of the mask or vent assembly defining the exhaust path to move to control the cross-sectional area of the exhaust path as a function of the pressure in the patient interface.

Figure 12:
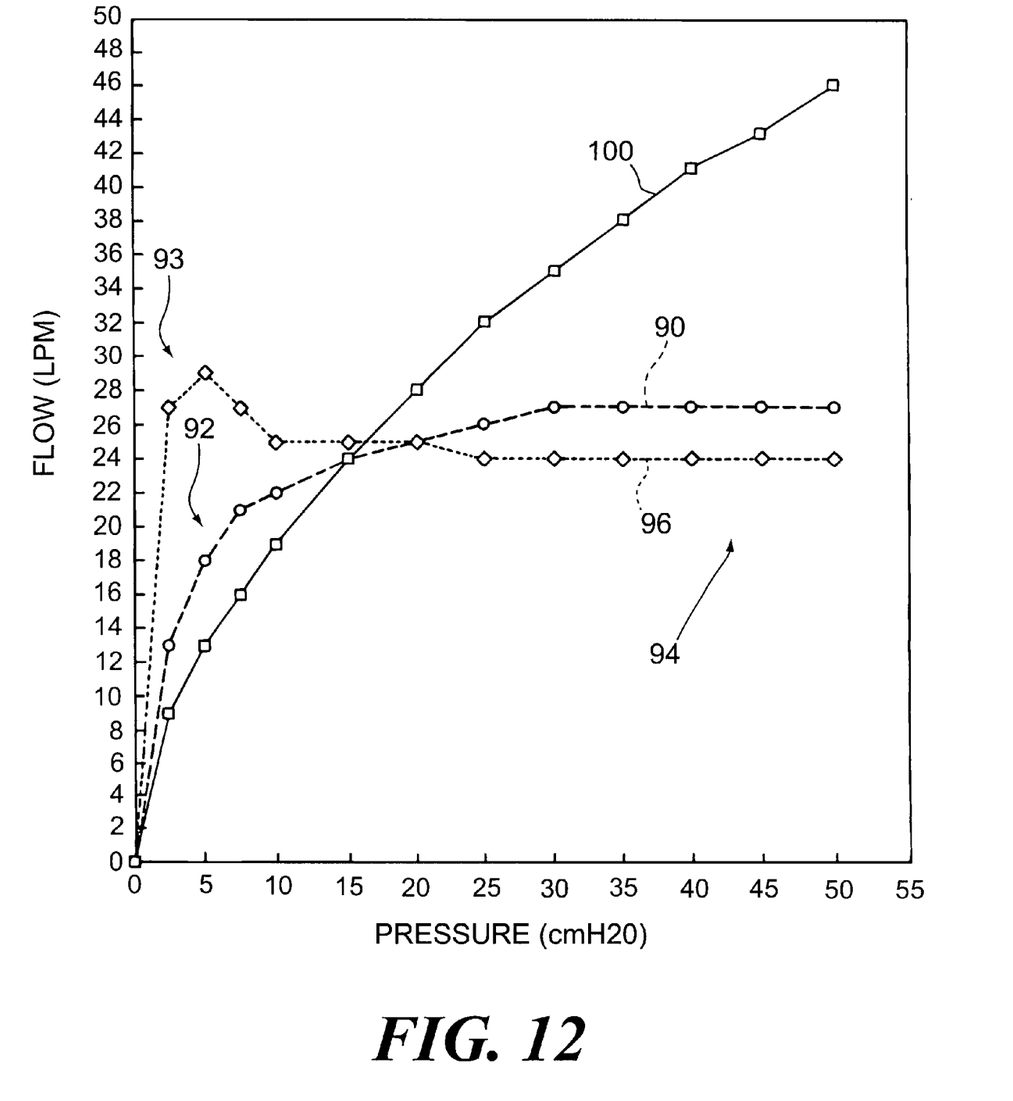
FIG. 12 is a graph illustrating the exhaust flow through the exhaust assembly of FIGS. 1–3 versus the flow through the a conventional exhaust assembly.

FIG. 12 is a graph illustrating the exhaust flow through the exhaust assembly of FIGS. 1–3 versus the flow through the conventional exhaust assemblies. In particular, curve 90 represents the flow of exhaust gas through exhaust assembly 33 of FIGS. 1–3. As indicated by area 92, the flow of gas through exhaust assembly 33 increases relatively smoothly as the pressure in interior space 16 increases and plateaus or level off, at area 94 so that the exhaust flow remains relatively constant even as the pressure increases. It can thus be appreciated that a relatively constant flow, i.e., ±2.5 liters per minute (1 pm), is maintained over a range of pressures, e.g. 7–22 cmH$_2$O, by exhaust assembly 33.

Curve 96 in FIG. 12 represents the flow of exhaust gas through the exhaust assembly taught by U.S. Pat. Nos. 5,685,296 and 5,937,855. Curve 96 also has a portion, indicated by area 94, where the flow of exhausts gas from a ventilation circuit remains relatively constant flow despite varying pressure in the ventilation circuit. However, curve 96, unlike curve 90 of the present invention, has a relatively abrupt change in flow over a relatively short change in pressure, as indicated by area 98. In short, the patient experiences are relative rapid change in flow until plateau portion of the curve is reached. The exhaust assembly of the present invention, avoids this abrupt transition, and, thereby, maximizes patient comfort by providing the relatively smooth flow transition in area 92 until the plateau portion of curve 90 is reached.

For the sake of completeness, a curve 100 is also shown in FIG. 12, which corresponds to the flow of exhaust gas through a conventional, fixed orifice, exhaust path. It can be appreciated that curve 100 does not include an plateau region, because, being a fixed size orifice, the cross sectional area of the exhaust path does not change with changes in the pressure in the patient circuit.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims.

What is claimed is:

1. A patient interface and exhaust assembly comprising:
    (1) a patient interface assembly comprising:
        (a) a faceplate having a first opening defined in a first end and a second opening defined in a second end thereof, and
        (b) a seal associated with the second opening for contacting a surface of a patient, wherein at least one of the faceplate and the seal define an interior of the patient interface assembly;
    (2) a patient circuit operatively coupled to the first opening to communicate a supply of breathing gas with the interior of the patient interface assembly; and
    (3) an exhaust assembly defined at an interconnection of the faceplate and patient circuit, wherein the exhaust assembly includes:
        (a) an exhaust path defined generally between the faceplate and the patient circuit so as to communicate the interior of the patient interface assembly with ambient atmosphere, and
        (b) a flow regulating member associated with the exhaust path to control a rate of flow of exhaust gas passing to atmosphere through the exhaust path by deforming the flow regulating member into the exhaust path, wherein a degree of deformation of the flow regulating member into the exhaust path increases as a pressure in the interior of the patient interface assembly increases relative to ambient atmospheric pressure.

2. An assembly according to claim 1, wherein the faceplate and the seal are separate structures that are combined to define the patient interface assembly.

3. An assembly according to claim 1, wherein the patient circuit is rotateably coupled to the faceplate.

4. An assembly according to claim 1, wherein the exhaust assembly includes multiple exhaust paths defined around a circumference of the patient circuit, and wherein the flow regulating member substantially surrounds the patient circuit so as be associated with each exhaust path in the plurality of exhaust paths to control a rate of flow of exhaust gas passing to atmosphere through each exhaust path.

5. An assembly according to claim 1, wherein the flow regulating member is a flexible membrane coupled to at least one of the faceplate and the patient circuit so as to alter a cross-sectional area of the exhaust path responsive to being deformed.

6. An assembly according to claim 5, wherein the exhaust path includes a first space defined between the flexible membrane and an inner surface of the faceplate and a second space defined between the patient circuit and the face plate.

7. An assembly according to claim 6, further comprising a swivel connector disposed at an end of the faceplate, wherein the exhaust path is further defined by an opening defined in the swivel connector.

8. A patient interface and exhaust assembly comprising:
   (1) a patient interface assembly comprising:
      (a) a faceplate having a first opening defined in a first end and a second opening defined in a second end thereof,
      (b) a seal associated with the second opening for contacting a surface of a patient, wherein at least one of the faceplate and the seal define an interior of the patient interface assembly;
   (2) a patient circuit operatively coupled to the first opening to communicate a supply of breathing gas with the interior of the patient interface assembly; and
   (3) an exhaust assembly defined in the faceplate, wherein the exhaust assembly includes:
      (a) an exhaust path defined in the faceplate so as to communicate the interior of the patient interface assembly with ambient atmosphere, and
      (b) a flow regulating member associated with the exhaust path to control a rate of flow of exhaust gas passing to atmosphere through the exhaust path by deforming the flow regulating member into the exhaust path, wherein a degree of deformation of the flow regulating member into the exhaust path increases as a pressure in the interior of the patient interface assembly increases relative to ambient atmospheric pressure.

9. An assembly according to claim 8, wherein the faceplate and the seal are separate structures that are combined to define the patient interface assembly.

10. An assembly according to claim 8, wherein the exhaust assembly includes multiple exhaust paths defined in the faceplate, and wherein the flow regulating member is fixed to the faceplate and associated with each exhaust path to control a rate of flow of exhaust gas passing to atmosphere through each exhaust path.

11. An assembly according to claim 8, wherein the flow regulating member is a flexible membrane coupled to the faceplate so as to alter a cross-sectional area of the exhaust path responsive to being deformed.

12. An assembly according to claim 11, wherein the exhaust path includes a first space defined between the flexible membrane and an inner surface of the faceplate and a second space defined between generally opposing surfaces of the faceplate.

13. An assembly according to claim 8, wherein the flow regulating member includes:
   a rigid member; and
   a deformable member coupled to the rigid member such that the rigid member is moveable to alter a cross-sectional area of the exhaust path responsive to the deformable member being deformed, and wherein at least one of the rigid member and the deformable member is coupled to the faceplate.

14. A patient interface and exhaust assembly comprising:
   (1) a patient interface assembly comprising:
      (a) a faceplate having a first opening defined in a first end and a second opening defined in a second end thereof,
      (b) a seal associated with the second opening for contacting a surface of a patient, wherein at least one of the faceplate and the seal define an interior of the patient interface assembly;
   (2) a patient circuit operatively coupled to the first opening to communicate a supply of breathing gas with the interior of the patient interface assembly; and
   (3) exhausting means for passing a substantially continuous flow of gas from the interior of the patient interface assembly to ambient atmosphere at a substantially constant flow rate irrespective of variations of pressure in the interior of the patient interface assembly relative to ambient atmosphere.

15. An assembly according to claim 14, wherein the faceplate and the seal are separate structures that are combined to define the patient interface assembly.

16. A system for providing a supply of breathing gas to an airway of a patient, comprising:
   (1) a pressure generator adapted to generate a flow of breathing gas;
   (2) a patient circuit having a first end operatively coupled to the pressure generator and a second end;
   (3) a patient interface assembly comprising:
      (a) a faceplate having a first opening defined in a first end and a second opening defined in a second end thereof, wherein the patient circuit is operatively coupled to the first opening,
      (b) a seal associated with the second opening for contacting a surface of a patient, wherein at least one of the faceplate and the seal define an interior of the patient interface assembly, and
   (4) exhausting means for passing a substantially continuous flow of gas from the interior of the patient interface assembly to ambient atmosphere at a substantially constant flow rate irrespective of variations of pressure in the interior of the patient interface relative to ambient atmosphere.

17. A system according to claim 16, wherein the faceplate and the seal are separate structures that are combined to define the patient interface assembly.

18. A system according to claim 16, wherein the exhausting means includes:
   an exhaust path defined generally between the faceplate and the patient circuit so as to communicate the interior of the patient interface assembly with ambient atmosphere; and
   a flow regulating member associated with the exhaust path to control a rate of flow of exhaust gas passing to atmosphere through the exhaust path by deforming the flow regulating member into the exhaust path, wherein a degree of deformation of the flow regulating member into the exhaust path is based on a pressure in the interior of the patient interface assembly relative to ambient atmospheric pressure.

19. A system according to claim 16, wherein the exhausting means includes:
   an exhaust path defined in the faceplate so as to communicate the interior of the patient interface assembly with ambient atmosphere; and
   a flow regulating member associated with the exhaust path to control a rate of flow of exhaust gas passing to atmosphere through the exhaust path by deforming the flow regulating member into the exhaust path, wherein a degree of deformation of the flow regulating member into the exhaust path is based on a pressure in the interior of the patient interface assembly relative to ambient atmospheric pressure.

20. Method of providing a supply of breathing gas to an airway of a patient, comprising:

generating a flow of breathing gas;

communicating, via a patient circuit, the flow of breathing gas to a patient interface assembly adapted to be donned by the patient, wherein the patient interface assembly includes a faceplate having a first opening defined in a first end and a second opening defined in a second end, and wherein the patient circuit is operatively coupled to the first opening, the patient interface assembly further comprising a seal associated with the second opening adapted to contact a surface of a patient for communicating the flow of breathing gas with an airway of a patient; and passing a substantially continuous flow of gas from the interior of the patient interface assembly to ambient atmosphere at a substantially constant flow rate irrespective of variations of pressure in the interior of the patient interface device relative to ambient atmosphere.

21. A method according to claim 20, wherein passing a substantially continuous flow of gas from the interior of the patient interface assembly to ambient atmosphere includes:

exhausting gas to ambient atmosphere through an exhaust path defined generally between the faceplate and the patient circuit; and controlling a rate of flow of exhaust gas passing to atmosphere through the exhaust path by causing a flow regulating member to deform into the exhaust path, wherein a degree of deformation of the flow regulating member into the exhaust path is based on a pressure in the interior of the patient interface assembly relative to ambient atmospheric pressure.

22. A method according to claim 20, wherein passing a substantially continuous flow of gas from the interior of the patient interface device to ambient atmosphere includes:

exhausting gas to atmosphere through an exhaust path defined in the faceplate; and controlling a rate of flow of exhaust gas passing to atmosphere through the exhaust path by causing a flow regulating member to deform into the exhaust path, wherein a degree of deformation of the flow regulating member into the exhaust path is based on a pressure in the interior of the patient interface assembly relative to ambient atmospheric pressure.

23. Method of providing a supply of breathing gas to an airway of a patient, comprising:

generating a flow of breathing gas;

communicating, via a patient circuit, the flow of breathing gas to a patient interface assembly adapted to be donned by the patient, wherein the patient interface assembly includes a faceplate having a first opening defined in a first end and a second opening defined in a second end, and wherein the patient circuit is operatively coupled to the first opening, the patient interface assembly further comprising a seal associated with the second opening adapted to contact a surface of a patient for communicating the flow of breathing gas with an airway of a patient;

exhausting gas to ambient atmosphere through an exhaust path defined generally between the faceplate and the patient circuit; and controlling a rate of flow of exhaust gas passing to atmosphere through the exhaust path by causing a flow regulating member to deform into the exhaust path, wherein a degree of deformation of the flow regulating member into the exhaust path is increases as a pressure in the interior of the patient interface assembly increases relative to ambient atmospheric pressure.

* * * * *